(12) United States Patent
Speier

(10) Patent No.: US 11,215,684 B2
(45) Date of Patent: Jan. 4, 2022

(54) METHOD FOR OBTAINING A MAGNETIC RESONANCE DATASET, STORAGE MEDIUM AND MAGNETIC RESONANCE APPARATUS

(71) Applicant: Siemens Healthcare GmbH, Erlangen (DE)

(72) Inventor: Peter Speier, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/883,118

(22) Filed: May 26, 2020

(65) Prior Publication Data

US 2020/0379067 A1 Dec. 3, 2020

(30) Foreign Application Priority Data

May 31, 2019 (EP) .................................. 19177582.4

(51) Int. Cl.
*G01R 33/36* (2006.01)
*A61B 5/055* (2006.01)
*G01R 33/56* (2006.01)

(52) U.S. Cl.
CPC .......... *G01R 33/3621* (2013.01); *A61B 5/055* (2013.01); *G01R 33/3607* (2013.01); *G01R 33/3692* (2013.01); *G01R 33/5608* (2013.01)

(58) Field of Classification Search
CPC ............ G01R 33/3607; G01R 33/3692; G01R 33/5608; A61B 5/055
See application file for complete search history.

(56) References Cited

U.S. PATENT DOCUMENTS 7,123,009 B1 * 10/2006 Scott .................. G01R 33/3621
324/311
2006/0244452 A1 11/2006 Den
2017/0160367 A1 6/2017 Schröter

FOREIGN PATENT DOCUMENTS

EP 3413075 A1 12/2018
WO WO2015197720 A1 12/2015

OTHER PUBLICATIONS

European Search Report for European Application No. 19177582.4-1022 dated Dec. 12, 2019.
Rigie, David et al: "Tracking Respiratory Motion Throughout Arbitrary MRI Sequences via Pilot Tone Navigation" Proceedings of the International Society for Magnetic Resonance in Medicine; ISMRM; Joint Annual Meeting ISMRM-ESMRMB; Paris, France; 16-21, No. 4108; Jun. 1, 2018.

* cited by examiner

*Primary Examiner* — Gregory H Curran
(74) *Attorney, Agent, or Firm* — Lempia Summerfield Katz LLC

(57) ABSTRACT

Storage medium, magnetic resonance apparatus and method for obtaining a magnetic resonance dataset including a pilot signal uses a magnetic resonance sequence. The pilot signal is generated at a first frequency range, and a magnetic resonance signal is generated at a second frequency range. The pilot signal and the magnetic resonance signal are acquired simultaneously. At least one parameter, in particular the phase and/or the frequency range, of the pilot signal is changed during the execution of the magnetic resonance sequence at least once.

19 Claims, 6 Drawing Sheets

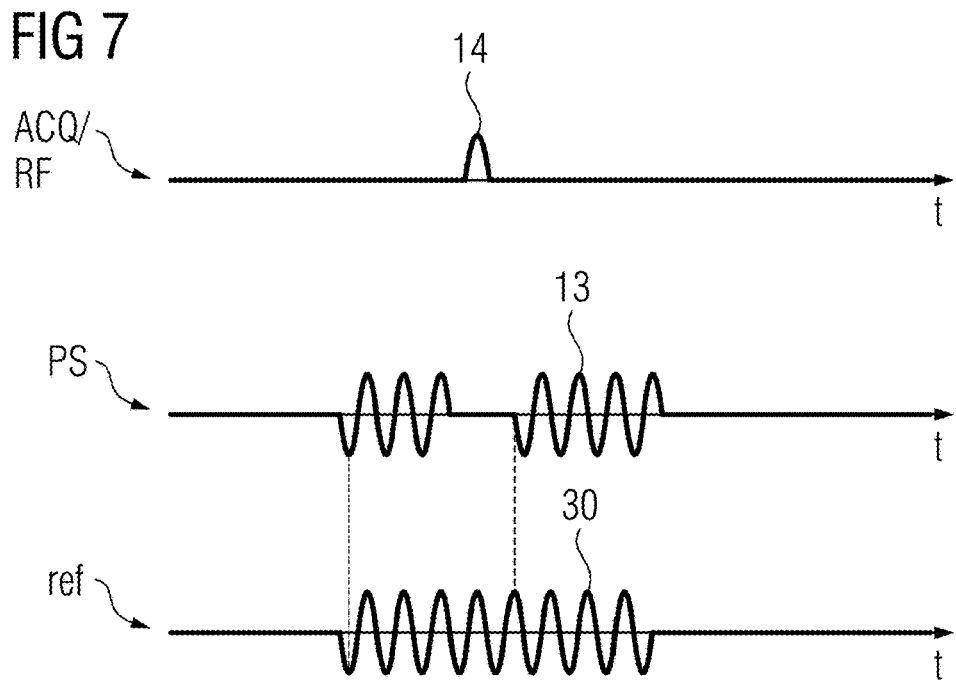
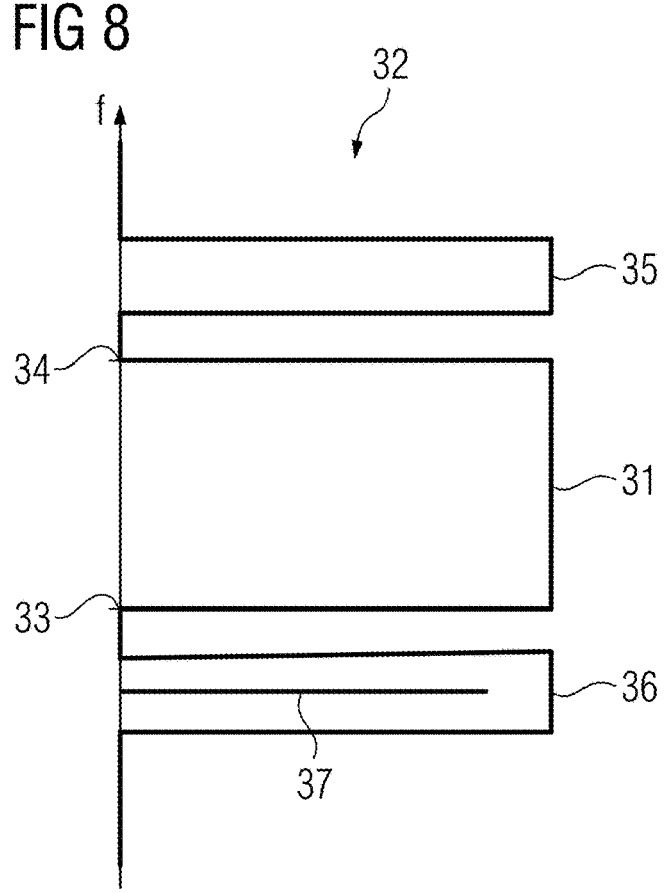

METHOD FOR OBTAINING A MAGNETIC RESONANCE DATASET, STORAGE MEDIUM AND MAGNETIC RESONANCE APPARATUS

RELATED CASE

This application claims the benefit of European Application EP19177582.4, filed on May 31, 2019, which is hereby incorporated by reference in its entirety.

FIELD

The present embodiments relate to obtaining a magnetic resonance dataset using a magnetic resonance sequence.

BACKGROUND

Magnetic resonance imaging (MRI) is a well-known technique using magnetic resonance (MR) to generate images of an examination object, e.g. a human body. Radio frequency (RF) signals having the Larmor frequency excite nuclear spins in the examination object. MR signals are generated due to the excitation. To generate images a spatial encoding of MR signals is to be used. This encoding is realized by using gradients to generate space-dependent resonance frequencies. The differing frequencies can then be taken to calculate the position from which the MR signal is coming.

Patient motion during the acquisition leads to a changed encoding and hence to a miscalculation of the signal position. This causes several artifacts depending on the type of motion and the magnetic resonance sequence.

There are several types of motion that can be differentiated. Firstly, there is bulk motion. Bulk motion describes the motion of the whole body of a patient or a whole part of the body, such as during the examination a leg is moved.

Secondly, there are flow artifacts. These are caused by a more or less constant flow depending on the body region. The greater the distance from the heart the more constant is the flow.

A third type of motion is periodic motion inside the body of the patient. Respiration and heartbeat are examples for the third type. Again, flow nearby the heart is a type of periodic motion.

There are different strategies to avoid artifacts caused by the different types of motion. To reduce flow artifacts during flow measurements, the flow gradient moment of the first order can be nulled. Also, a flow compensation can be applied.

Additionally, it is known to track the motion, and then to adjust the signal according to a starting or reference position. Navigator echoes can be used for this purpose. Then movements can be corrected in the signals of an MR data set.

Furthermore, electrocardiography (ECG) signals can be used to trigger the data acquisition. Usually the R-wave is used to start an acquisition. Normally several heartbeats are necessary to gather a complete dataset, therefore the examination is segmented. All segments start in the same phase of the heart cycle because of the trigger.

A fourth way to track motion and/or trigger an acquisition is the usage of a pilot signal. A pilot signal is also called pilot tone in MR literature and is a magnetic signal having a frequency nearby the MR signal and within the receiver bandwidth. Then the MR signal and the pilot signal can be acquired simultaneously, and the pilot signal can be used as a reference to calculate movements.

The pilot signal can be created with an additional signal source, e.g. a second antenna. The signal can be applied independent of the RF pulses. Motion inside the body affects the amplitude, frequency and/or phase of the pilot signal and can be used to determine the occurrence and/or the strength of the motion.

EP 3 413 075 A1 teaches to separate the simultaneously acquired pilot signal and MR signal, to assign a physiological phase to the pilot signal and to set time points used for triggering and/or data processing.

Using a pilot signal simplifies the motion detection compared to ECG because there is no need to train staff to attach the ECG sensor at the right positions.

Unfortunately, a pilot signal can cause sometimes an artifact of its own. The pilot signal, which is originally distinct from the MR signal, can be compromised by non-linearities in the receive path that generate harmonics and produce side bands. If the side bands lie within the MR frequency band, a single pixel can be brightened up in an image processed from the MR data set.

Therefore, there is a need for obtaining a dataset including a pilot signal having a reduced "pilot signal artifact".

SUMMARY AND DETAILED DESCRIPTION

These needs are satisfied in a method for obtaining a magnetic resonance dataset including a pilot tone signal using a magnetic resonance sequence having the acts:
a) generating a pilot signal at a first frequency range, b) generating a magnetic resonance signal at a second frequency range, c) acquiring the pilot signal and the magnetic resonance signal simultaneously, characterized in that at least one parameter, in particular the phase and/or the frequency range, of the pilot signal is changed during the execution of the magnetic resonance sequence at least once.

The main aspect is to distribute the pilot signal artifact along the spatial directions determined by the spatial encoding variation and thus become less conspicuous.

The pilot signal is applied during the MR examination. The frequency range of the pilot signal usually has of a single frequency. The application of the pilot signal is independent of that of the RF pulses. The pilot signal can be applied before, during and/or after an RF pulse. The frequency range of the pilot signal and the MR signal do not overlap. However, the pilot signal may be mixed with other signals present in the receiving system or if non-linear processes create overtones during the receive process. This creates the pilot signal artifact as described above during reception.

The MR signals may be echo signals or free induction decay (FID) signals. In particular, in chemical shift imaging, images are created using FIDs. In either case the MR signals are acquired simultaneously with the pilot signals whereas the generation of the signals is independent, as described above.

The change of the pilot signal parameter or parameters happens during its transmission. Therefore, the transmitted pilot signal already has the changed parameters. As described above, the pilot signal is changed always by motion after transmission, this change cannot be affected but is to be tracked.

The magnetic resonance apparatus has at least two antennas to transmit the signals. One of them is for the generation of the pilot signals and the second for the generation of the RF pulses. One of the antennas may be also be used to receive the pilot signals and the MR signals.

The frequency areas where the pilot signals and the MR signals lie within are usually called "frequency bands". Here the term frequency range is used to define that different bands can be used. In particular the frequency band of the pilot signal can be changed several times. The range of each signal may include bands that do not overlap. The band of the pilot signal usually contains only one frequency. If the frequency changes, also the frequency band of the pilot signal changes and has no overlap to the foregoing frequency band. Hence the area of the possible frequencies for the pilot signal is called frequency range.

The RF pulses and the pilot signals are used within a magnetic resonance sequence. A magnetic resonance sequence generally is a given sequence of RF pulses, magnetic field gradients, delays and acquisition windows. This sequence defines the signal behavior during the acquisition. There are many known sequences like FLASH (Fast Low-Angle SHot), TSE (Turbo Spin Echo), FISP (Fast Imaging with Steady state Precession), and so on.

In an imaging sequence, acts a) and c) are repeated as often as FIDs or k-space lines are acquired. Act a) includes a generation by RF pulses or by gradient echoes.

A magnetic resonance sequence usually has of many partial measurements. Except for one shot sequences, a magnetic resonance sequence has a multitude of excitation cycles. An excitation cycle lasts one repetition time $T_R$. In an excitation cycle, a part of the k-space is sampled. In particular, a segmented measurement has several partial measurements. One segment includes at least one excitation cycle. For example, a TSE measurement is segmented in phase encoding direction if the k-space is not sampled in one shot but in several acts.

Usually the only difference between two excitation cycles of a magnetic resonance sequence is a change of the strength of the phase encoding gradients.

Act b) can be repeated as often as acts a) and c). In case of multi gradient-echo sequences, it may be repeated only once for each echo train.

Regarding the signal acquisition, some features are explained further:

An excitation pulse is used to excite the magnetization. Its flip angle usually is between 0° and 90°. Regarding spin echo sequences and gradient echo sequences, the flip angle is exactly 90°. Fast gradient echo sequences may have smaller flip angles. The excitation pulse also is used to define the length of the repetition time TR, which is the length of one excitation cycle. Each scan sequence has at least one excitation pulse otherwise there was no signal.

In the following it is referred to a change of several parameters of the pilot signal. Of course, only one parameter could be changed as well.

Preferably, the parameters of the pilot signal are changed at least once in an excitation cycle. Moreover, the parameters of the pilot signal may be changed exactly once in an excitation cycle.

Alternatively, the parameters of the pilot signal may be changed exactly once for each acquired MR signal. This is important in case of multi echo sequences as EPI (Echo Planar Imaging) or TSE.

Advantageously the parameters of the pilot signal are changed if a predetermined sequence event occurs. A magnetic resonance sequence consists of many repeating excitation cycles as described above. Then all elements of the sequence occur at the same point of time in an excitation cycle. One or more of these events can be used as an occasion to change one or more parameters of the pilot signal.

Preferably, the parameters of the pilot signal are changed if a predetermined RF pulse is applied. This could be an excitation pulse or a refocusing pulse.

Advantageously, the parameters of the pilot signal are changed always at the same point of time within an excitation cycle. In particular, the first RF pulse of an excitation cycle can be used to change the parameter or parameters of the pilot signal. That simplifies the tracking of changes in the parameters of the pilot signal. It additionally simplifies the sequence structure.

Preferably, the parameters of the pilot signal are changed during the application of an RF pulse. In this duration, the receiver is closed and the pilot signal cannot be acquired anyhow. Hence, there is neither additional time required for the parameter change nor a loss of information.

Alternatively, the parameters of the pilot signal may be changed independent to sequence events. Hence, they are changed asynchronously to sequence events, in particular to the repetition time TR. To do so, random time points can be chosen. Furthermore, a clock can be used to trigger an asynchronous change.

Advantageously, the parameters of the pilot signal are saved. When a pilot signal or an MR signal is saved, additional data can be added to form a data package. Then, the pilot signal is part of a data package. One of the additional data to be saved may be the current parameters of the pilot signal.

Alternatively, the current parameters or parameter change is impressed on the pilot signal. For example, the complex pilot signal could be rotated by the negative of the current phase to generate a phase variation. The use of the data packages is basically preferred because the pilot signal has not to be changed to transport additional data. Otherwise the creation and handling of data packages can be avoided.

Advantageously, the phase of the pilot signal is one of the parameters being changed. In particular the phase may be the only parameter of the pilot signal being changed.

Preferably, the phase of the pilot signal is calculated according to a quadratic phase cycle. This is known from RF spoiling. There the phase is incremented quadratically using a recursive formula. In particular the phase change may be a multiple of a fixed phase $\Psi$. Preferred values for $\Psi$ are 50° and 117°. The n-th phase $\varphi_n$ of the pilot signal is calculated according to:

$$\varphi_n = \alpha + \Sigma n*(n-1)*\Psi \text{ with } n=1,2,3,\ldots$$

$\alpha$ is the phase at the beginning, e.g. 0°. In each excitation cycle, the phase change is increased.

Alternatively, the phase of the pilot signal is changed randomly. To generate the random numbers, a pseudo random number generator can be implemented.

Furthermore, the phases of the pilot signal can be specified by the magnetic resonance sequence. In case of a sequence using RF spoiling and hence a quadratic phase cycle for the RF pulses, the phase cycle for the pilot signal can be adapted depending on the RF phase cycle.

In the embodiments, the goal is that the series of phases of the pilot signal and the receiver during acquisition of one image are non-coherent, i.e., as different as possible. Then, the brightening is distributed over one image line at a fixed frequency. If the frequency of the pilot signal is changed as well, the pilot signal artifact is distributed over all frequencies.

To generate a difference between the phases of the pilot signal and the receiver also, the receiver phase can be changed according to a quadratic phase cycle. To have a difference between the phases of the pilot signal and the receiver the phase constant $\Psi_r$ for the receiver is 50° and the phase constant $\Psi_p$ for the pilot signal is 117°. The respective phases can be calculated using the formula shown above. The choice of the phase constant $\Psi_p$ may be in particular dependent on the magnetic resonance sequence in use. If one or more of the RF pulses of the sequence use a quadratic phase cycle, the phase constant $\Psi_p$ for the pilot signal has to be chosen in a way that no coherences occur. Otherwise, if none of the RF pulses of the sequence uses a quadratic pulse cycle, a default value, e.g. 117°, may be used for the phase constant $\Psi_p$.

The calculation of the phases can be executed before the execution of a sequence. For example, the phase values can be stored in lists. These lists may have e.g. 256 or 512 entries, and the phases to be used can be extracted.

Alternatively, the phases can be calculated during the execution of a magnetic resonance sequence, e.g. by using the above-mentioned formula. Then they can be adopted to constraints.

In accordance with another aspect, a magnetic resonance apparatus is disclosed comprising: an MR data acquisition scanner including two radio-frequency transmitters and an RF receiver and a gradient coil arrangement, a memory in which parameter sets are stored, a computer having access to said memory and being configured to read said parameter sets from said memory, and said computer being configured to carry out the method described above.

Each of the embodiments described with regard to the method also can be realized in the magnetic resonance apparatus.

In accordance with another aspect, a non-transitory computer-readable data storage medium encoded with programming instructions is disclosed. Said storage medium is loaded into a computer system of a magnetic resonance (MR) apparatus that includes an MR data acquisition scanner having two radio-frequency (RF) transmitters, an RF receiver, a gradient coil arrangement, and a memory. Said programming instructions cause said computer system to carry out the method described above.

Each of the embodiments described with regard to the method also can be realized in the data storage medium.

Further details are provided below.

BRIEF DESCRIPTION OF THE DRAWINGS

Parts that correspond to one another are labeled with the same reference characters in all figures.

FIG. 7 shows an example phase change of the pilot signal,

FIG. 8 shows example first and second frequency ranges, and

DETAILED DESCRIPTION OF THE PREFERRED EMBODIMENTS

Figure 1:
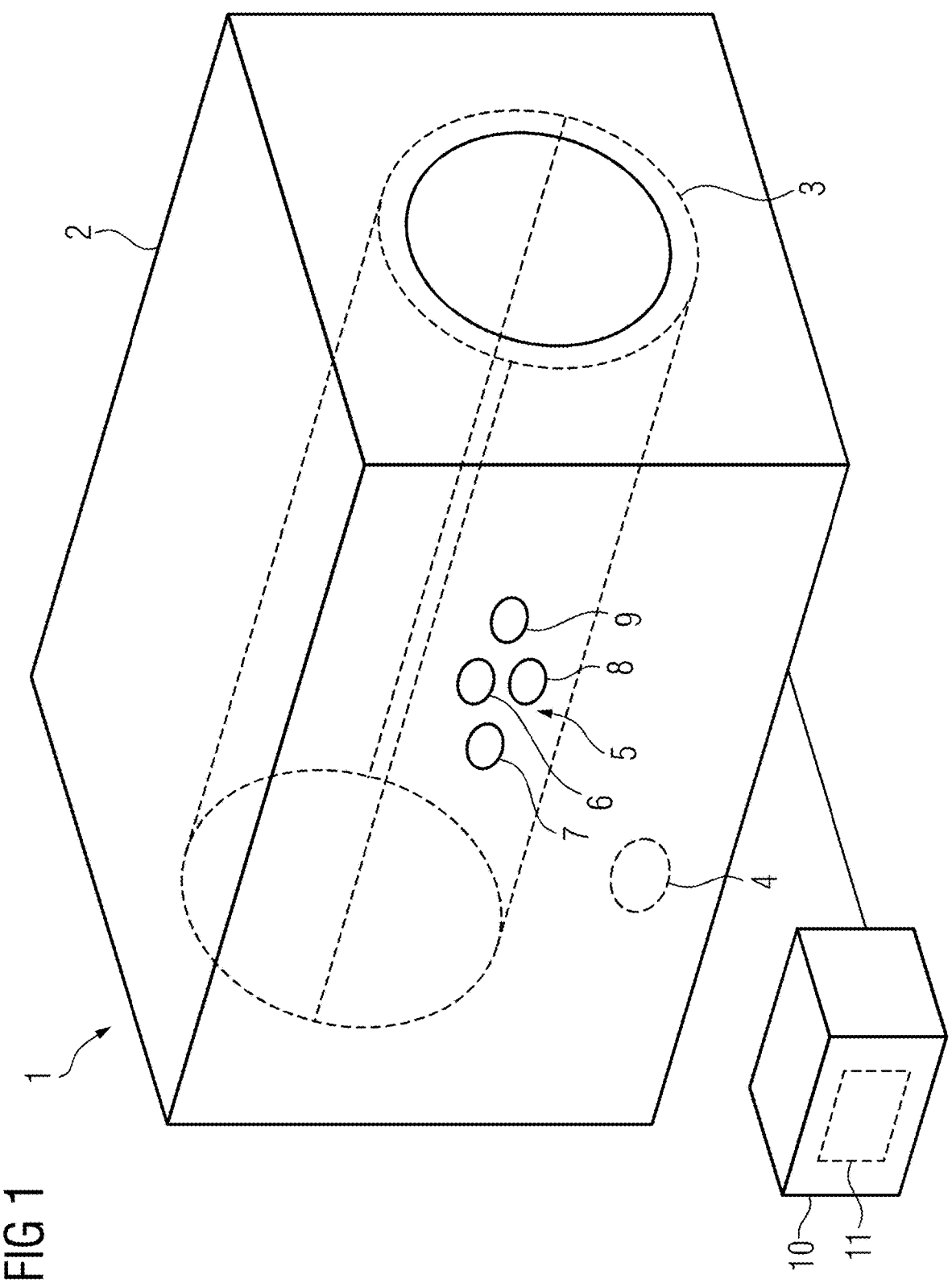
FIG. 1 shows an embodiment of a magnetic resonance apparatus.

FIG. 1 shows a magnetic resonance apparatus 1. The magnetic resonance apparatus 1 has a scanner 2. A first transmit coil arrangement 3 is part of the scanner 2. The first transmit coil arrangement 3 is used to generate the pilot signals in a first frequency range.

Furthermore, the magnetic resonance apparatus 1 has a second transmit coil arrangement 4, which is usually designed as a body coil, and thus has a single coil. The second transmit coil arrangement is used to generate RF pulses in a second frequency range.

The first frequency range and the second frequency range both lie within the receiver bandwidth but have no overlap.

Furthermore, the magnetic resonance apparatus 1 has a reception coil arrangement 5. The reception coil arrangement 5 is a coil array with coils 6, 7, 8 and 9. To enable the coils 6, 7, 8 and 9 to be distinguished more easily, the transmit coil arrangements 3 and 4 are shown by a dashed outline.

A control computer 10 controls the operation of the magnetic resonance apparatus 1.

The magnetic resonance apparatus 1 also has a non-transitory data storage medium 11 as part of the control computer 10 or independent thereof, on which computer code for carrying out magnetic resonance measurements is stored.

The coil array 5 is used only to read out the measurement signal, which can be an echo signal. The coils 6, 7, 8 and 9 of the coil array 5 read out the measurement signal at the same time. Instead of the coil array 5, an individual coil can also be used as the detection coil for individual embodiments.

Further components of the magnetic resonance apparatus 1, such as gradient coils and a patient bed are not shown, for clarity.

Figure 2:
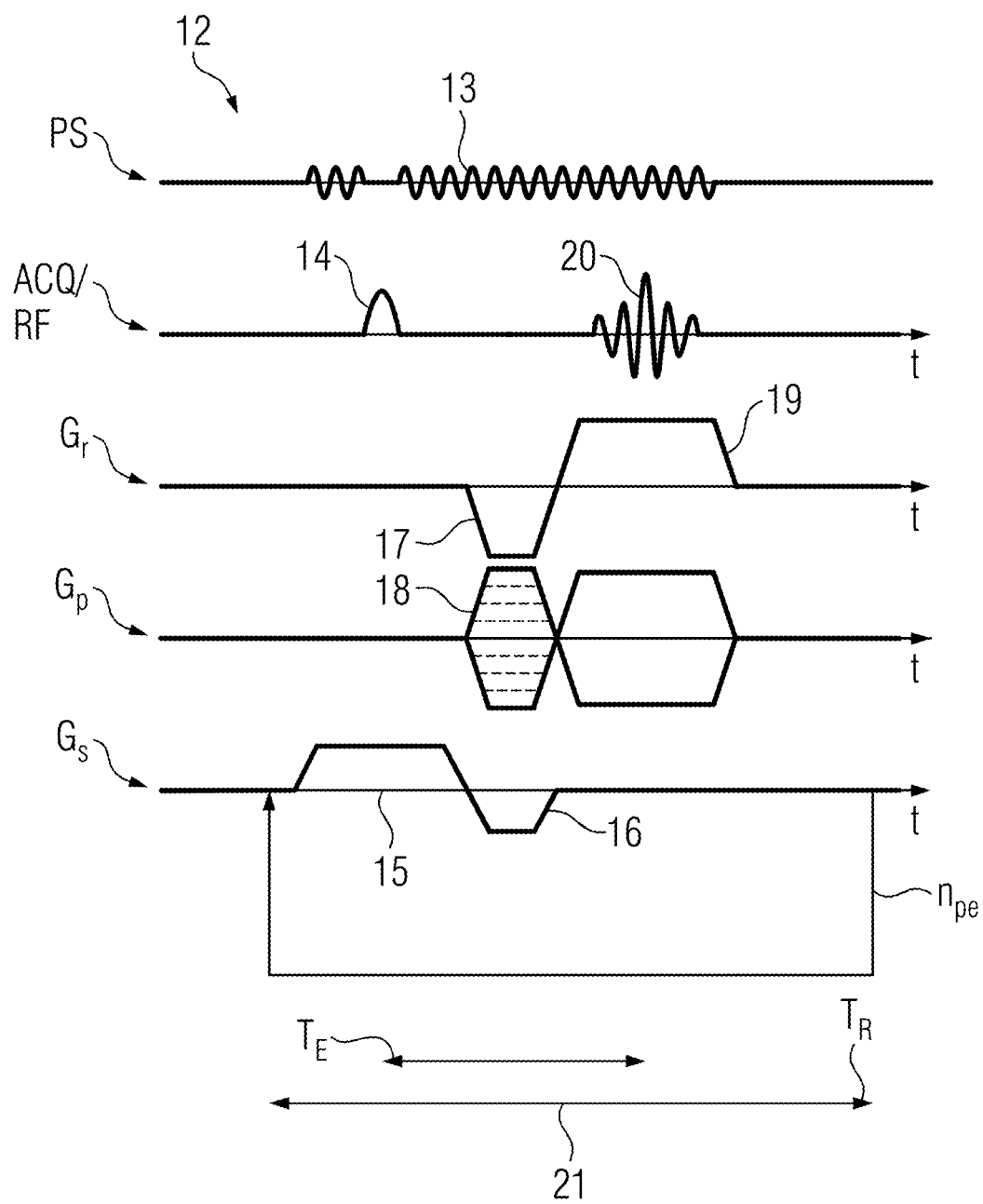
FIG. 2 shows an example sequence diagram of a magnetic resonance sequence.

FIG. 2 shows an exemplary sequence diagram 12 of a FLASH sequence. Axis PS shows the pilot signal, axis RF the RF pulses and acquisition windows, axis $G_r$ the gradients in read direction, axis $G_{pe}$ the gradients in phase encoding direction and axis $G_s$ the gradients in slice selection direction.

The pilot signals 13 may be applied all the time after the excitation pulse 14. The excitation pulse 14 is the only RF pulse applied in the shown sequence diagram 12. Slice selection gradient 15 is applied at the same time to select a defined slice in a patient. It is known to use an additional slice rephrasing gradient 16 to compensate the dephasing fraction of the slice selection gradient 15.

A dephasing gradient 17 in readout direction may be applied along with the slice rephrasing gradient 16 to get a minimal echo time $T_E$. Further, the phase encoding gradient 18 may be applied at the same time.

In readout direction $G_r$ a readout gradient 19 is applied after the dephasing gradient 17. This generates a gradient echo 20, which is acquired. Simultaneously, the pilot signal 13 is measured.

All acts beginning at one excitation pulse, here RF pulse 14, to the next excitation pulse are part of an excitation cycle 21. The length of an excitation cycle is the repetition time $T_R$.

The excitation cycle is repeated $n_{pe}$ times, one repetition for one k-line of k-space if no coil array is used for sampling the echo signals. In case of coil arrays, the number of excitation cycles is reduced.

The FLASH sequence is only used to show the dependencies of changes of the parameters of the pilot signal 13 to sequence events. Of course, other sequences could be used as well.

Figure 3:
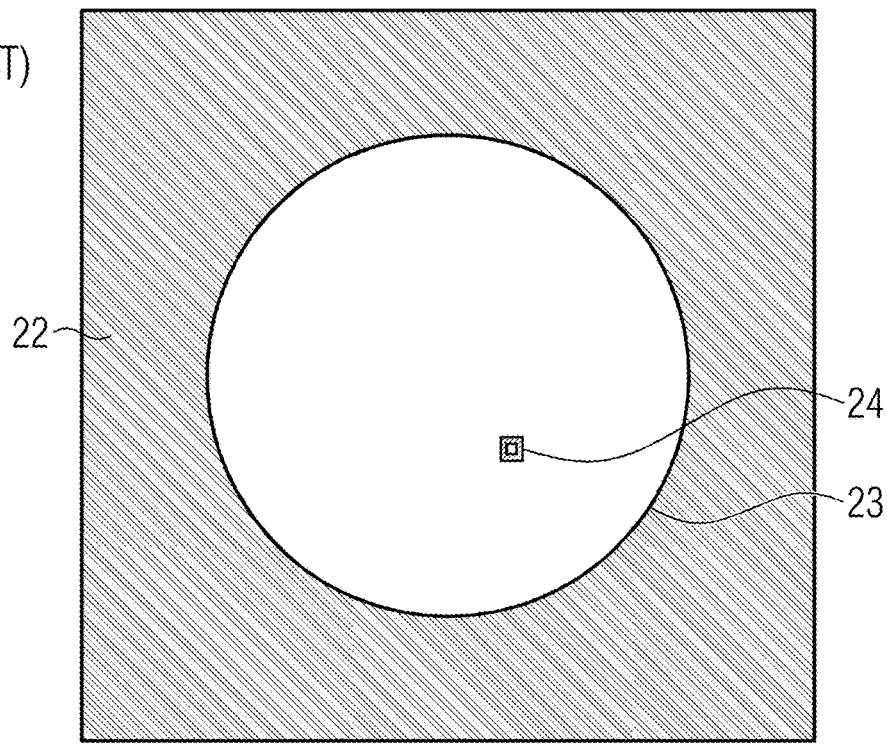
FIG. 3 shows a first example magnetic resonance image.

If the pilot signal 13 has a single frequency and the phase is held coherent to the acquisition phase of the receiver, this can result in a bright spot as shown in FIG. 3.

FIG. 3 shows a first magnetic resonance image 22.

Image 22 may have been acquired using the sequence according to FIG. 2. Basically, a pilot signal has to be used during the acquisition. In image 22, an exemplary water tube 23 is shown. If the phase of the pilot signal 13 is held coherent to the acquisition phase of the receiver and the frequency of the pilot signal is not changed either, a bright spot 24 may occur in image 22. The bright spot is a single pixel having a signal intensity higher than the surrounding water due to the pilot signal 13. The phase encoding direction named $k_y$ and the read direction $k_x$ are shown as well.

Figure 4:
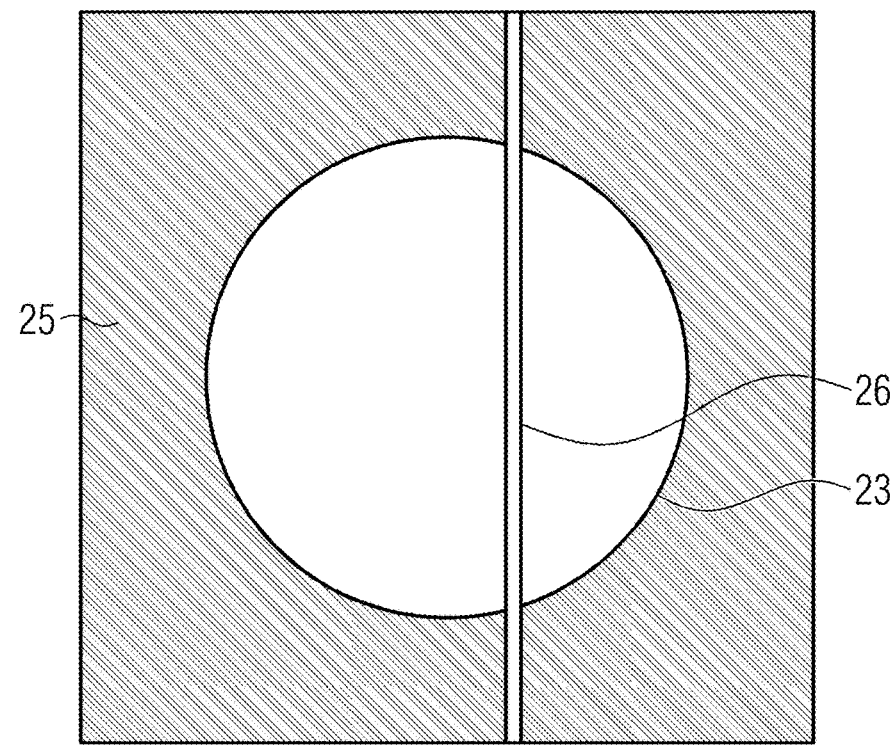
FIG. 4 shows a second example magnetic resonance image.

FIG. 4 shows a second magnetic resonance image 25. During the acquisition of the raw data of image 25, the phase of the pilot signal 13 has been changed according to one of the alternatives shown above. E.g. a quadratic phase cycle for the pilot signal with $\Psi_p=50°$ and one for the receiver phase with $\Psi_r=117°$ has been used. Hence there is no bright spot but a brighter line 26. The difference between the bright line 26 and the water signal in the water tube 23 is much lower than between the bright spot 24 and the water signal.

To change the phase of the pilot signal 13, the duration of the excitation pulse 14 has been used. In this duration no signal can be acquired. Therefore, the time can be used for the phase change without information loss.

Changing the phase this way, there is a new phase for each excitation cycle 21.

Figure 5:
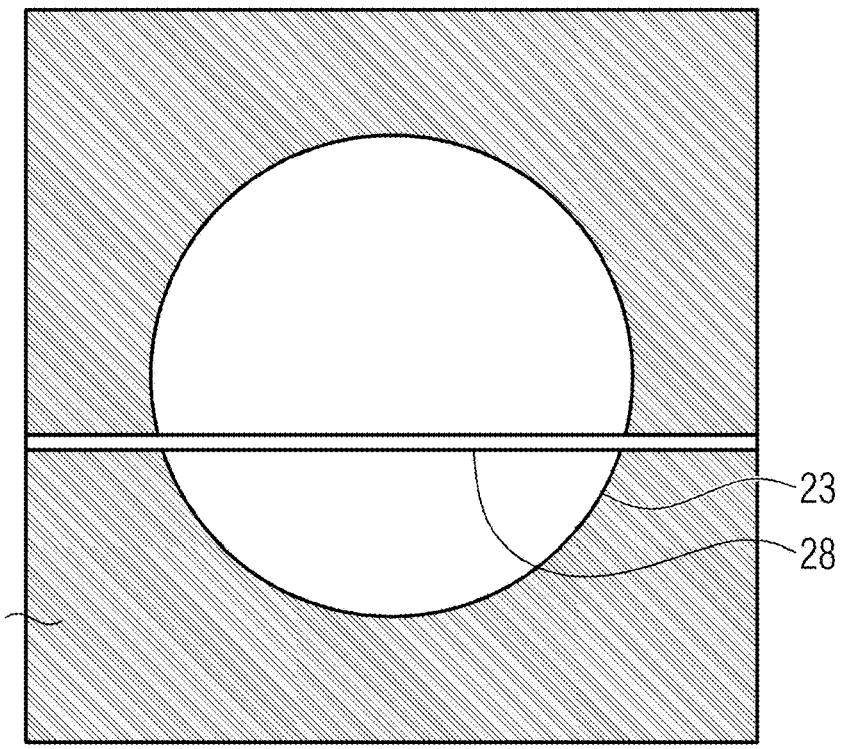
FIG. 5 shows a third example magnetic resonance image.

FIG. 5 shows a third magnetic resonance image 27 showing again the water tube 23. During the acquisition of the raw data of image 27, the transmission phase and the transmission amplitude of the pilot signal have been kept constant, but the frequency has been changed. Here again the frequency may be changed for each excitation cycle. This leads to a brighter line 28 which extends in read direction $k_x$ which is frequency encoded.

Figure 6:
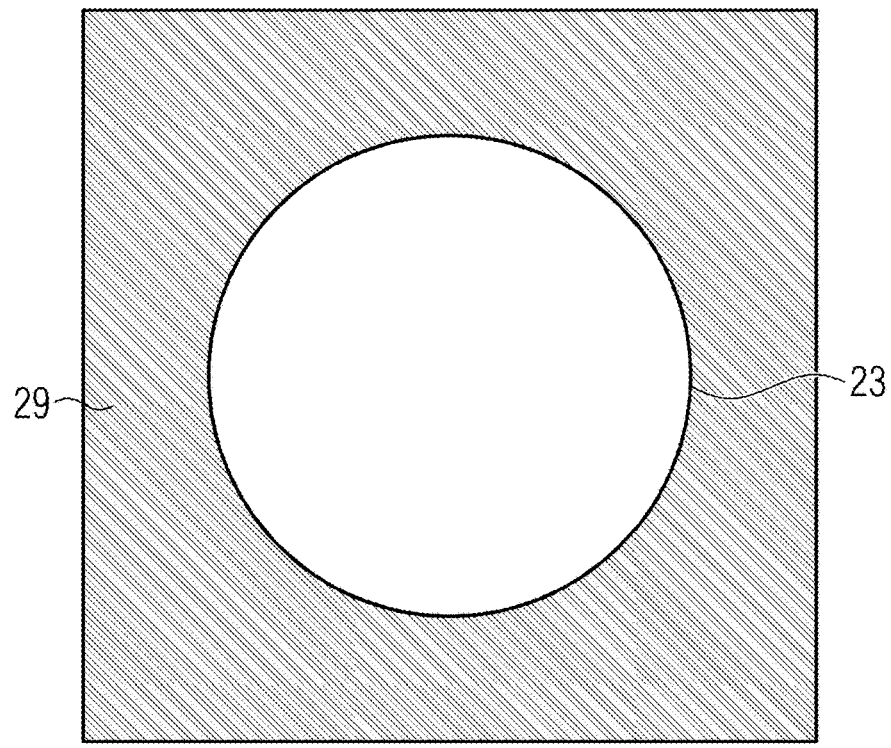
FIG. 6 shows a fourth example magnetic resonance image.

FIG. 6 shows a fourth magnetic resonance image 29 showing again the water tube 23. During the acquisition of the raw data of image 29, only the transmission amplitude of the pilot signal has been kept constant, while the frequency and the phase of the pilot signal 13 have been changed. Here again change has happened in each excitation cycle. This leads to a brightening of the whole image 29.

Of course, the acquired raw data have been processed in a known way, e.g. using a Fourier transform to get the images 22, 25, 27 and 29.

FIG. 7 shows the realization of a phase-locked phase change. There, a reference phase 30 is used to track a reference phase position. During an RF pulse 14 the phase of the pilot signal 13 can be changed to a predetermined value. FIG. 7 shows a change of 117° and the first change in a quadratic phase cycle. These values can be calculated before an examination for typical parameters. The number of phase encoding acts often is 128, 256 or 512. Then lists of phase values for $\Psi_p=50°$ and $\Psi_r=117°$ and $n_{pe}=512$ can be stored in the storage medium 11. It is not necessary to store lists for 128 or 256 phase encoding acts, because they are included as the first 128 and 256 values in the list with 512 acts.

FIG. 8 shows two frequency ranges 31 and 32. The second frequency range 31 is the range of the magnetic resonance signal and is a simple band having a starting frequency 33 and a final frequency 34.

The first frequency range 32, the range of the pilot signal 13, may have subranges 35 and 36 including a number of single frequencies 37. Alternatively, the second frequency range 32 may include only one of the subranges 35 or 36. Moreover the second frequency range 32 may only include a single frequency 37. In this case, the frequency of the pilot signal 13 is constant and only the phase of the pilot signal 13 is changed. During transmission, only one of the frequencies in the second frequency range 32 is used for the pilot signal 13. If the frequency is changed as described above the frequencies 37 of the second frequency range 32 are used one by one.

Independent of the construction of the ranges 31 and 32, the ranges 31 and 32 do not overlap.

Figure 9:
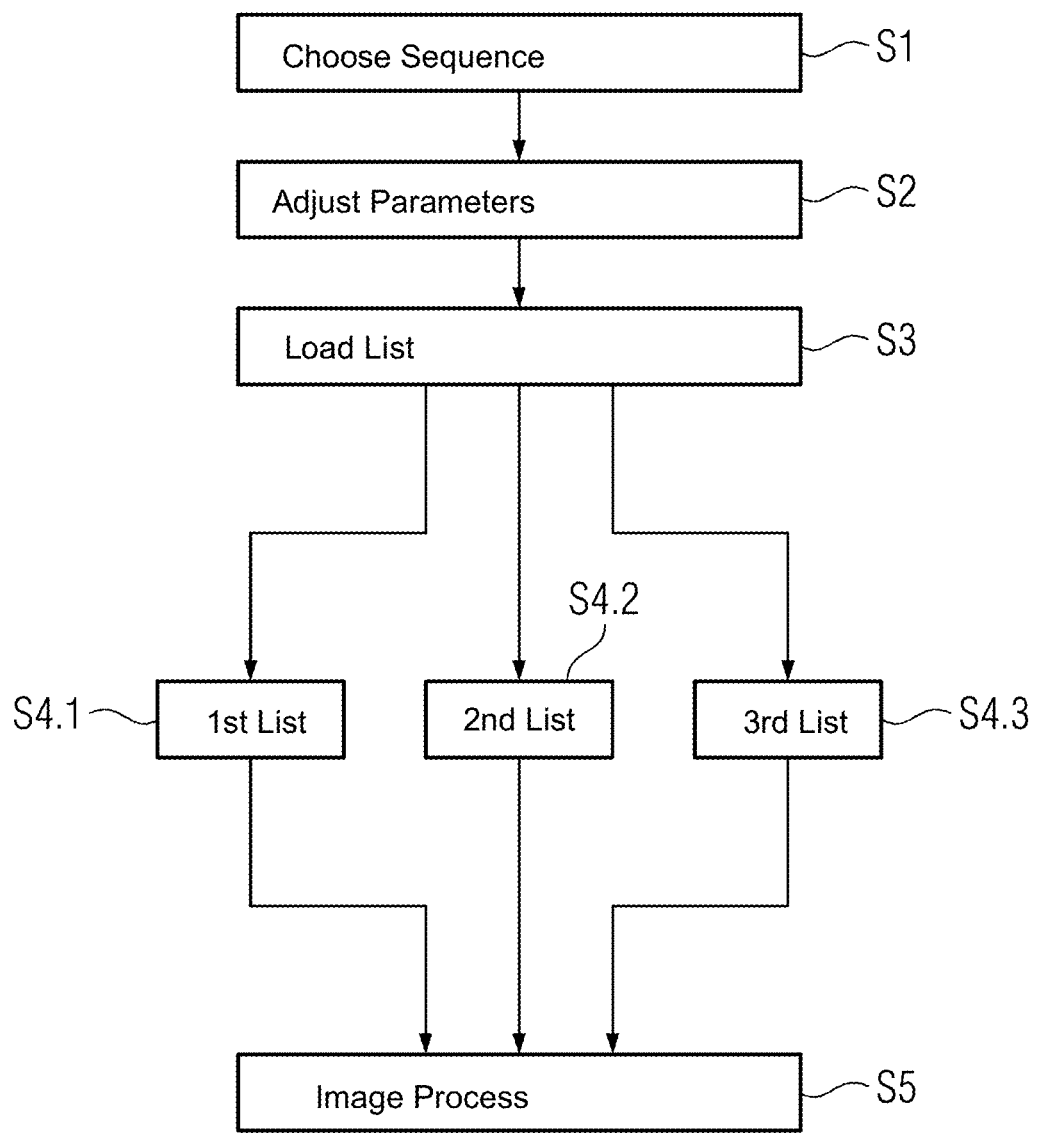
FIG. 9 is a procedure diagram of changing phases of pilot signals, according to one embodiment.

FIG. 9 shows a procedure diagram of obtaining a magnetic resonance dataset including a pilot signal using a magnetic resonance sequence. In act S1, the sequence is chosen. For example, a FLASH sequence having a sequence diagram as shown in FIG. 2 is taken. This sequence uses RF spoiling.

In act S2, the parameters of the FLASH sequence are adjusted. Parameters usually to be adjusted are the resolution, the echo time $T_E$, the flip angle $\alpha$ of RF pulse 14, and so on.

Depending on acts 1 and 2, in act 3, one of a number of stored lists with precalculated phases is loaded into the working memory of computer 10. For example, one of the lists has been calculated using $\Psi=50°$, a second list using $\Psi=117°$ and a third list using pseudo random numbers.

Depending on the choice of act 3, one of acts 4.1 to 4.3 is executed. In act 4.1, the first list is used, in act 4.2, the second list, and in act 4.3, the third list.

After the acquisition of all MR signals and pilot signals including phase and/or frequency changes of the pilot signal, the data set is processed to an image as shown in FIGS. 4 to 6.

Although the invention has been illustrated and described in detail by the preferred exemplary embodiment, it is not limited by the disclosed examples and a person skilled in the art can derive other variations here from without departing from the scope of the invention. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

The invention claimed is:

1. A method for obtaining a magnetic resonance dataset, the method including a pilot signal using a magnetic resonance sequence, the method comprising:
    a) generating a pilot signal at a first frequency range,
    b) generating a magnetic resonance signal at a second frequency range, and
    c) acquiring the pilot signal and the magnetic resonance signal simultaneously, wherein at least one parameter of the pilot signal is changed during the execution of the magnetic resonance sequence at least once, wherein the at least one parameter of the pilot signal is changed when a predetermined sequence event occurs, the predetermined sequence event comprising a predetermined RF pulse being applied.

2. The method of claim 1, wherein the at least one parameter of the pilot signal is changed at a point of time within an excitation cycle.

3. The method of claim 1, wherein the at least one parameter of the pilot signal is changed during the application of an RF pulse.

4. The method of claim 1, wherein at least one parameter of the pilot signal is saved.

5. The method of claim 4, wherein parameters including the at least one parameter of the pilot signal and the pilot signal are saved in a data package.

6. The method of claim 4, wherein the current phase or phase change is impressed on the pilot signal.

7. The method of claim 1, wherein the at least one parameter of the pilot signal is changed at least once in each excitation cycle.

8. The method of claim 1, wherein the change of a phase of the pilot signal is calculated according to a quadratic phase cycle.

9. The method of claim 8, wherein the phase (Y) is chosen dependent on the magnetic resonance sequence.

10. The method of claim 8, wherein the phase act (Y) is 50° or 117°.

11. The method of claim 1, wherein a phase of the pilot signal is changed randomly.

12. The method of claim 1 wherein the at least one parameters is a frequency range.

13. A non-transitory computer-readable data storage medium encoded with programming instructions, said storage medium being loaded into a computer system of a magnetic resonance apparatus that comprises an MR data acquisition scanner having two RF transmitters, an RF receiver, a gradient coil arrangement, and a memory, said programming instructions causing said computer system to:
generate a pilot signal at a first frequency range,
generate a magnetic resonance signal at a second frequency range, and acquire the pilot signal and the magnetic resonance signal simultaneously, wherein at least one parameter of the pilot signal is changed during the execution of the magnetic resonance sequence at least once, wherein the at least one parameter of the pilot signal is changed when a predetermined sequence event occurs, the predetermined sequence event comprising a predetermined RF pulse being applied.

14. The non-transitory computer-readable data storage medium of claim 13, wherein the at least one parameter is a phase and/or a frequency range.

15. A magnetic resonance apparatus comprising:
an MR data acquisition scanner comprising two RF transmitters, an RF receiver, and a gradient coil arrangement,
a memory in which parameter sets are stored,
a computer having access to said memory and being configured to read said parameter sets from said memory, and
said computer being configured to generate a pilot signal at a different frequency range than a magnetic resonance signal and acquire the pilot signal and the magnetic resonance signal simultaneously, wherein at least one parameter of the pilot signal is changed during the execution of the magnetic resonance sequence at least once, wherein the computer is configured to change the at least one parameter of the pilot signal when a predetermined sequence event occurs, the predetermined sequence event comprising a predetermined RF pulse being applied.

16. The magnetic resonance apparatus of claim 15 wherein the at least one parameter comprises a phase.

17. The magnetic resonance apparatus of claim 16 wherein the change of the phase of the pilot signal is calculated according to a quadratic phase cycle.

18. The magnetic resonance apparatus of claim 15 wherein the at least one parameter comprises a frequency.

19. A method for obtaining a magnetic resonance dataset, the method including a pilot signal using a magnetic resonance sequence, the method comprising:
a) generating a pilot signal at a first frequency range,
b) generating a magnetic resonance signal at a second frequency range, and
c) acquiring the pilot signal and the magnetic resonance signal simultaneously, wherein at least one parameter of the pilot signal is changed during the execution of the magnetic resonance sequence at least once, wherein the change of the pilot signal is a change in a phase of the pilot signal calculated according to a quadratic phase cycle.

* * * * *